(12) United States Patent
Wallmann et al.

(10) Patent No.: US 10,625,019 B2
(45) Date of Patent: Apr. 21, 2020

(54) FILLING AID

(71) Applicant: Transcoject GmbH, Neumünster (DE)

(72) Inventors: Stefan Wallmann, Hamburg (DE); Jochen Heinz, Flintbek (DE); Dieter Schilling, Aukrug (DE)

(73) Assignee: TRANSCOJECT GMBH, Neumünster (DE)

( * ) Notice: Subject to any disclaimer, the term of this patent is extended or adjusted under 35 U.S.C. 154(b) by 0 days.

(21) Appl. No.: 15/763,712

(22) PCT Filed: Sep. 19, 2016

(86) PCT No.: PCT/DE2016/200437
§ 371 (c)(1),
(2) Date: Mar. 27, 2018

(87) PCT Pub. No.: WO2017/054812
PCT Pub. Date: Apr. 6, 2017

(65) Prior Publication Data
US 2018/0272067 A1    Sep. 27, 2018

(30) Foreign Application Priority Data
Sep. 29, 2015 (DE) .......................... 10 2015 218 723

(51) Int. Cl.
*A61M 5/178* (2006.01)
*A61M 1/20* (2006.01)
(Continued)

(52) U.S. Cl.
CPC ............ *A61M 5/1782* (2013.01); *A61J 1/201* (2015.05); *A61J 1/2065* (2015.05); *A61J 1/2096* (2013.01);
(Continued)

(58) Field of Classification Search
CPC ........ A61M 5/1782; A61M 5/24; A61M 5/28; A61M 2209/045; A61J 1/201; A61J 1/2065; A61J 1/2096; A61J 1/06
See application file for complete search history.

(56) References Cited

U.S. PATENT DOCUMENTS 4,338,980 A    7/1982  Schwebel et al.
4,434,820 A *  3/1984  Glass ................. A61M 5/1782
                                                        141/100
(Continued)

FOREIGN PATENT DOCUMENTS

EP          1 757 320 A1    2/2007
WO      2005/011781 A1      2/2005
WO      2011/109915 A1      9/2011

*Primary Examiner* — Marina A Tietjen
(74) *Attorney, Agent, or Firm* — McGlew and Tuttle, P.C.

(57) ABSTRACT

A filling aid is provided for filling a cylinder ampule (7) with a medical or pharmaceutical fluid. The filling aid in a common housing (4) includes a first receiver (24) which is configured for receiving the cylinder ampule (7) to be filled, and a second receiver (26) which is configured for receiving a receptacle (18) containing a medical or pharmaceutical substance. A first access opening (28) is formed on the first receiver (24) and is arranged such that the first access opening (28) lies opposite an opening of a cylinder ampule (7) when this cylinder ampule is inserted into the first receiver (24). A second access opening (30) is formed on the second receiver (26) and is arranged such that the second access opening (30) lies opposite an opening of a receptacle (18) when this receptacle (18) is inserted into the second receiver (26).

17 Claims, 10 Drawing Sheets

(51) Int. Cl.
  *A61M 1/06*   (2006.01)
  *A61M 5/24*   (2006.01)
  *A61M 5/28*   (2006.01)
  *A61J 1/20*   (2006.01)
  *A61J 1/06*   (2006.01)

(52) U.S. Cl.
  CPC .................. *A61M 5/24* (2013.01); *A61J 1/06* (2013.01); *A61M 5/28* (2013.01); *A61M 2209/045* (2013.01)

(56) References Cited

U.S. PATENT DOCUMENTS

| | | | | |
|---|---|---|---|---|
| 4,475,915 A | | 10/1984 | Sloane | |
| 5,329,976 A | * | 7/1994 | Haber | A61J 1/2089 141/18 |
| 5,356,380 A | * | 10/1994 | Hoekwater | A61J 1/2089 285/4 |
| 5,566,729 A | * | 10/1996 | Grabenkort | A61J 1/2089 141/25 |
| 8,100,154 B2 | * | 1/2012 | Reynolds | A61J 1/2089 141/319 |
| 8,512,308 B2 | * | 8/2013 | Yokoyama | A61J 1/16 604/403 |
| 9,636,277 B2 | * | 5/2017 | Foshee | A61J 1/2096 |
| 2002/0004643 A1 | * | 1/2002 | Carmel | A61J 1/2089 604/86 |
| 2007/0088315 A1 | * | 4/2007 | Haindl | A61J 1/2089 604/411 |
| 2012/0238969 A1 | * | 9/2012 | Ruegg | A61K 8/64 604/290 |
| 2012/0298254 A1 | * | 11/2012 | Brem | A61J 1/2096 141/18 |
| 2016/0144105 A1 | * | 5/2016 | Hooven | A61M 5/152 604/132 |

* cited by examiner

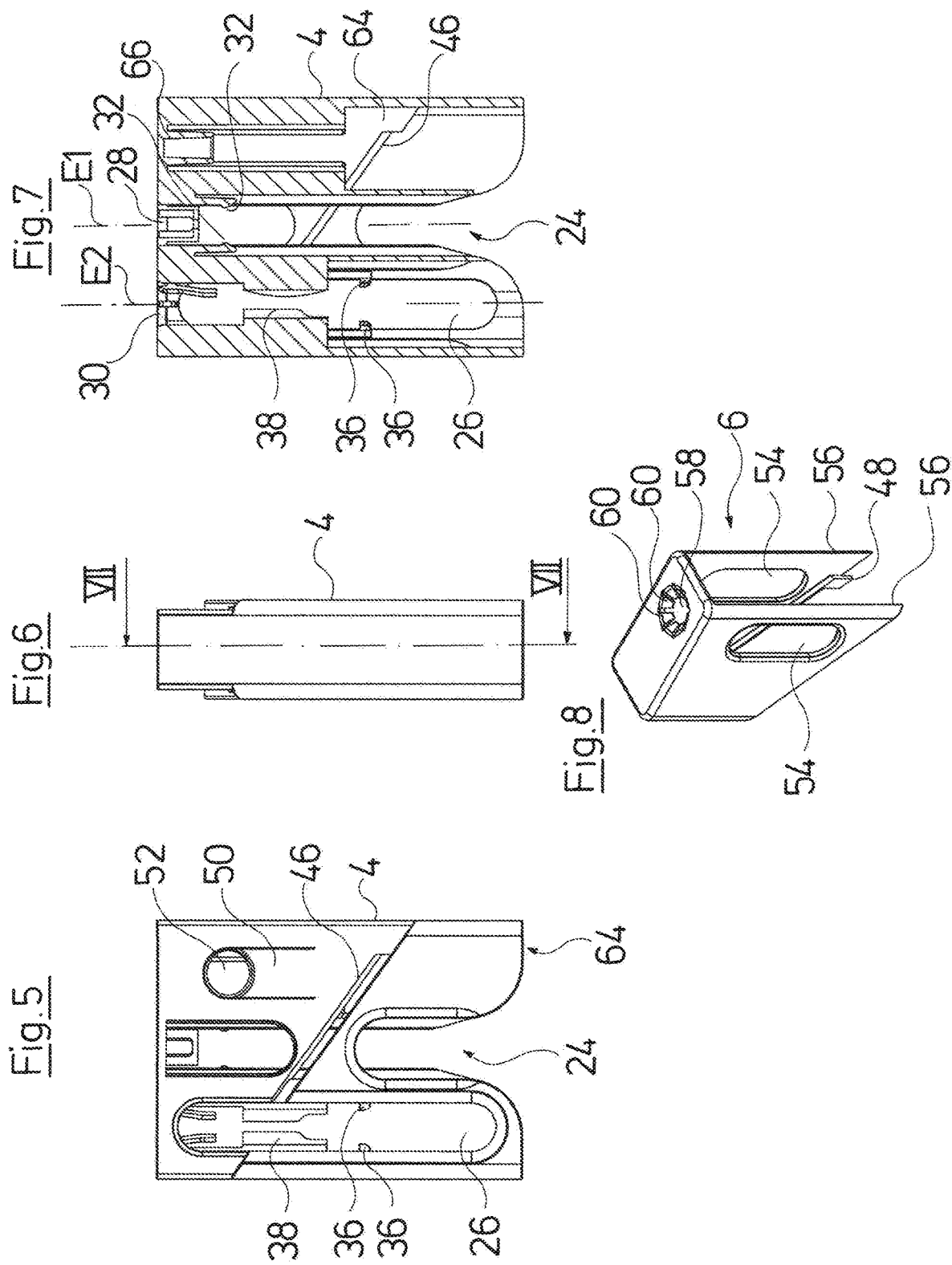

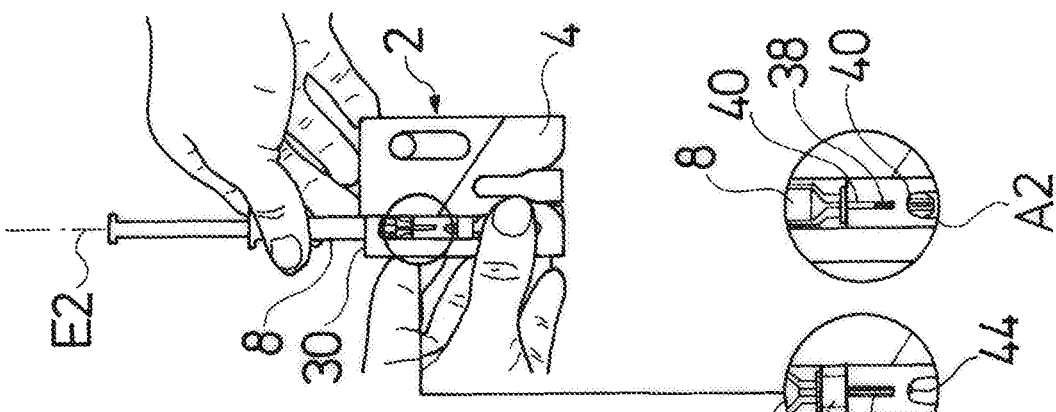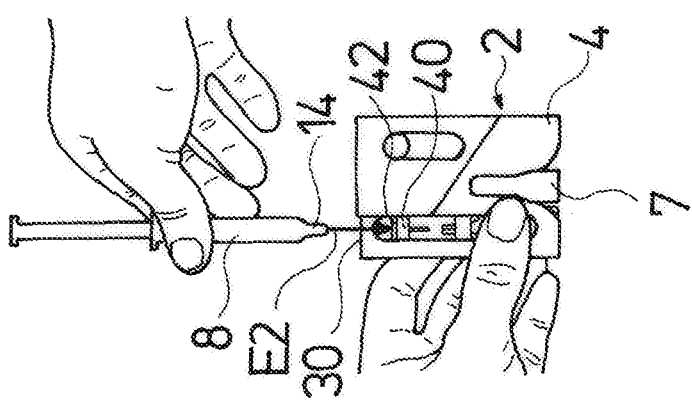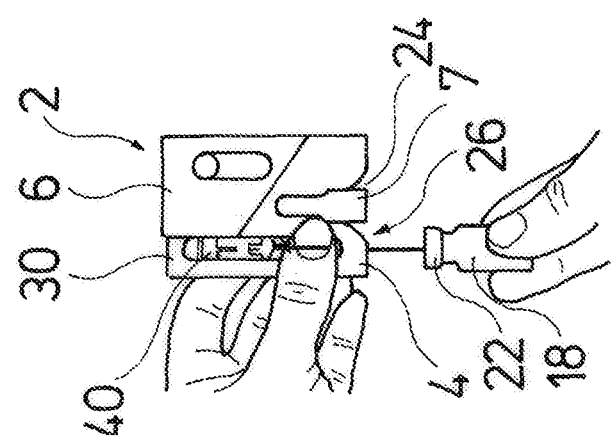

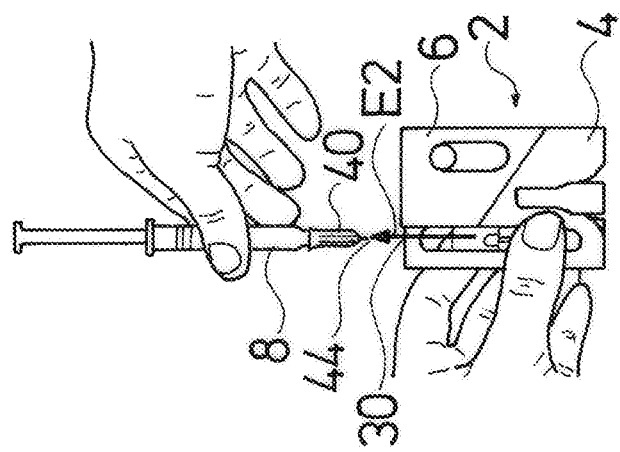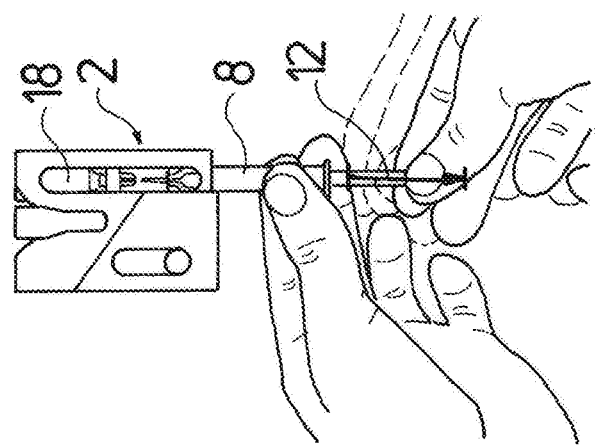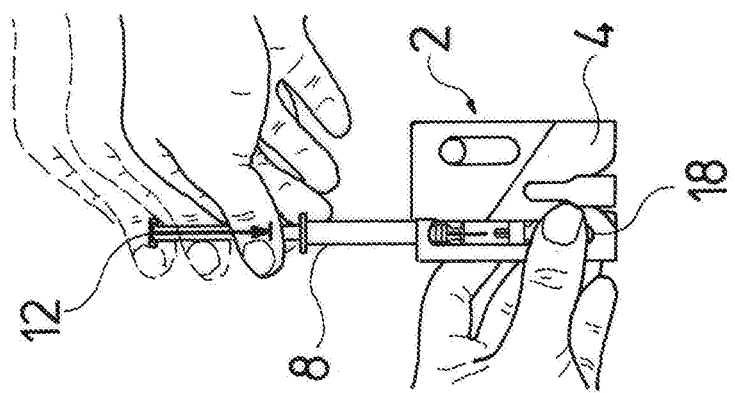

FILLING AID

CROSS REFERENCE TO RELATED APPLICATIONS

This application is a United States National Phase Application of International Application PCT/DE2016/200437, filed Sep. 19, 2016, and claims the benefit of priority under 35 U.S.C. § 119 of German Application 10 2015 218 723.3 filed, Sep. 29, 2015, the entire contents of which are incorporated herein by reference.

FIELD OF THE INVENTION

The invention relates to a filling aid for filling a cylinder ampule as well as to a method for filling a cylinder ampule whilst using such a filling aid.

BACKGROUND OF THE INVENTION

In various medical applications, it is necessary to transfer a medical or pharmaceutical fluid from a receptacle into cylinder ampule, a co-called carpule. This is particularly the case if the mentioned fluid must be dissolved beforehand from a dry medical or pharmaceutical substance, in particular present in a powder-like manner, by way of adding a fluid solvent, such as saline solution or water, for injection purposes.

Such cylinder ampules or carpules are particularly applied in so-called pen systems or carpule syringes which can also be provided for home use. In particular, such pen systems are known for insulin, but can also be applied for other medical or pharmaceutical active substances, for example hormone preparations for children and young adults. As a rule, these are present in powder form and must firstly be dissolved in the manner mentioned above and then transferred into a cylinder ampule or carpule, in order to then insert these into the carpule syringe or the pen system. This is not always simple, particularly for medical novices. In particular, it is problematic to maintain the necessary sterility with these procedures.

SUMMARY OF THE INVENTION

With regard to this problem, it is an object of the invention to provide a filling aid for filling a cylinder ampule, said filling aid permitting the transfer of a medical or pharmaceutical fluid from a receptacle into a cylinder ampule or carpule in a simple manner.

The filling aid according to the invention serves for transferring a medical or pharmaceutical fluid from a receptacle, in which this fluid is provided or mixed, into a cylinder ampule. This filling aid can be applied for the most varied of medical or pharmaceutical fluids.

The filling aid according to the invention, as an essential element comprises at least one holding aid. This comprises a housing, in which a first receiver is formed. This first receiver is configured so as to receive the cylinder ampule to be filled. This means that the receiver is dimensioned and shaped such that a cylinder ampule which is to be filled and concerning which it is preferably a cylinder ampule for common cylinder ampule syringes, can be received. Such cylinder ampules are available on the market under the description carpule. A second receiver is also provided in the housing and is configured to receive a receptacle, in which the medical or pharmaceutical fluid is provided. This means that the second receiver is dimensioned and shaped such that a common receptacle for receiving a medical or pharmaceutical substance can be inserted into it and received in it. In particular, this receptacle is a common vial. Instead of providing the medical or pharmaceutical fluid in ready form in the receptacle; the receptacle can also comprise a medical or pharmaceutical substance which must firstly be dissolved with a solvent to be added, such as saline solution or water, in order to thus produce the medical or pharmaceutical fluid. Herein, this dissolving is preferably effected in the filling aid, i.e. in a condition, in which the receptacle is received in the second receiver.

A first access opening is formed on the first receiver. This is arranged and configured such that it lies opposite an opening of a cylinder ampule, when this ampule is inserted into the first receiver. I.e. the opening or a septum of an inserted cylinder ampule which closes this opening is accessible from the outside through the first access opening, so that the cylinder ampule which is arranged in the housing of the filling aid can be filled through this first access opening.

Furthermore, the housing comprises a second access opening which is arranged on the second receiver. This second access opening is configured and situated such that it lies opposite an opening or a closure of a receptacle which closes the opening, when this receptacle is inserted into the second receiver. I.e. the opening or the closure (e.g. a septum) of the receptacle, when this receptacle is inserted into the second receiver, is accessible through the second access opening so that a solvent for example, for dissolving a powder, can be brought into the receptacle and/or the contents of the receptacle can be removed from this, through the second access opening.

This design of the filling aid according to the invention has the advantage that the two elements, between which the medical or pharmaceutical fluid is to be transferred, can be reliably held in one component, specifically the holding aid. The filling aid can therefore simultaneously hold the receptacle, in which the fluid is to be mixed or provided, and the cylinder ampule to be filled. The handling is simplified by way of this, since the transfer of the fluid from the receptacle into the cylinder ampule can then be filled for example with the help of a syringe which is firstly inserted into the second access opening, in order to receive the contents of the receptacle into the syringe. The syringe can subsequently be re-stuck from the second access opening into the first access opening and the contents can then be transferred out of the syringe into the cylinder ampule. The filling aid or its holding aid thereby holds the cylinder ampule and the receptacle, in particular such that their openings are protected and contaminations are prevented. After the transfer of the fluid into the cylinder ampule, this ampule can then be removed from the first receiver and inserted for example into a carpule syringe or a conventional pen system. Such a design is not only advantageous for the application by the patient himself, but also on use e.g. in clinics, doctors surgeries and laboratories.

The housing of the filling aid according to the invention is preferably formed from plastic and is further preferably configured as a single-part and in particular single-piece plastic component. In particular, the housing can be manufactured as an injection molded part of plastic, which permits an inexpensive manufacture.

Fixation means which are configured and envisaged to releasably fix a cylinder ampule in the receiver are preferably provided in the first receiver. The fixation means are preferably configured for holding a common, i.e. standardized cylinder ampule or carpule. The fixation means are configured and arranged such that they fixedly hold the cylinder ampule in the receiver when a syringe is inserted through the first access opening, in order to fill the cylinder ampule. Furthermore, the fixation means are however configured such that the cylinder ampule can be removed from the receiver. For this, the cylinder ampule can be gripped and a force exerted upon the cylinder ampule, said force exceeding a holding force of the fixation means. The direction of removal of the cylinder ampule from the first receiver thereby preferably extends in the longitudinal direction of the cylinder ampule. This is further preferably simultaneously also the insertion direction, in which a syringe can be inserted into the first access opening, in order to come into connection with the opening of the cylinder ampule, so as to bring a fluid out of the syringe into the cylinder ampule. The fixation means are preferably configured as non-positive-fit and/or positive-fit fixation elements which preferably grip the cylinder ampule at its front end, i.e. the end which is adjacent to the opening. Further preferably, the fixation means can be configured as a latching hooks or latching tongues. In particular, the latching hooks or latching tongues can engage around or behind a collar which surrounds the opening. Herein, the latching hooks or the latching tongues are preferably arranged such that given an adequately large force action in the longitudinal direction of the cylinder ampule, they are deflected out of their latching position and release the cylinder ampule. Such latching tongues or latching hooks are preferably configured in a single-part manner, further as one piece with at least a part of the housing, preferably with the complete part of the housing. In particular, latching hooks or latching tongues can be co-formed in a simple manner on manufacturing the housing of plastic.

According to a particularly preferred embodiment, the filling aid is configured such that a cylinder ampule is preassembled and releasably fixed in the first receiver by the fixation means as well as is removable out of the first receiver. The filling aid is thus delivered to the user in this preassembled condition, so that the user no longer needs to insert the cylinder ampule into the filling aid. This has the advantage that the handling is further simplified and the cylinder ampule is fixed in the filling aid in a reliable and protected manner.

According to a further preferred embodiment, fixation means which are configured and envisaged to fix a receptacle containing a medical or pharmaceutical substance, in the receiver, preferably in a releasable manner, are arranged in the second receiver. Such a receptacle is a vial which is common in the medical field. I.e., the fixation means are preferably dimensioned and configured such that they can fix such a vial. The fixation by way of the fixation means is preferably releasable in a manner such that the receptacle can be removed from the receiver whilst releasing the fixation, by way of an adequate application of force. Herein, the removal direction is preferably situated such that it corresponds to the longitudinal axis or middle axis of the receptacle which preferably likewise corresponds to the insertion direction of a syringe into the second access opening. The fixation means are preferably configured as latching hooks or latching tongues which engage behind the receptacle at a collar. In the case of common receptacles, such a collar is formed at that axial end, at which the opening is situated, and surrounds and/or holds the closure of the receptacle. The latching tongues or latching hooks are preferably formed as one piece or one part with at least one part of the housing, preferably with the complete housing. These latching hooks can therefore be inexpensively manufactured together with the housing by way of injection molding. The latching hooks or latching tongues are preferably configured such that given an adequately large force action upon the receptacle, they move out of their locking position into a released position, so that the receptacle can be removed from the receiver. However, is further preferably also possible to deliver the receptacle with the medical or pharmaceutical substance or the medical or pharmaceutical fluid separately, so that it must firstly be inserted by the user into the second receiver and there is latched and/or clamped preferably by the fixation means. The receptacle can remain in the receiver after the medical or pharmaceutical fluid has been taken from the receptacle in the aforementioned manner, since it is no longer required. Alternatively, it can also be removed from the receiver again by the user, for example for the separate disposal, inasmuch as the fixation means in the second receiver are configured for a releasable fixation.

According to a further preferred embodiment, a cannula element is releasably held in the second receiver. This cannula element can comprise a cannula and a Luer connection. Herein, the cannula element is arranged in the second receiver such that the Luer connection of the cannula faces the second access opening and the cannula is directed such that it penetrates into a receptacle which is inserted into the second receiver. The cannula element serves for penetrating with its cannula into the opening of the receptacle and in particular for piercing a seal, for example a septum, in the opening of the receptacle.

Particularly preferably, the cannula element in the second receiver is arranged in a linear guide which permits a movement of the cannula element in its longitudinal direction, i.e. in the longitudinal direction of the cannula. Herein, the cannula element is movable in the linear guide between a first and a second position, wherein in the first position the cannula element is situated closer to the second opening than in its second position. The second position is thereby situated such that in this position, the cannula penetrates into the receptacle, i.e. in particular pierces a septum of the receptacle. In the initial position, i.e. in the delivered condition of the filling aid, the cannula element is preferably situated in the first position, in which the cannula does not penetrate into the part of the receiving space, in which the receptacle is received. An arresting or clamping for the cannula element in the first position is preferably provided, wherein such can be overcome by a force action. On use, a syringe with a Luer cone is inserted into the second access opening such that the Luer cone engages with the Luer connection of the cannula. On further insertion of the syringe into the second access opening, the cannula element is moved out of its first position into its second position, wherein preferably a present arresting or clamping is overcome. The cannula element with the cannula is thus pushed into the receptacle.

Further preferably, at least one holding means which releasably fixes the cannula element is arranged in the second receiver, wherein the holding means preferably produces a holding force in the longitudinal direction of the cannula, said holding force being smaller than a force which can be transmitted by the Luer connection in the longitudinal direction, i.e. a transmittable tension force. The holding means can simultaneously assume the function of the aforementioned arresting or clamping. The holding means prevents the cannula element from being able to fall out of the second access opening. On use, the cannula element together with the syringe is pulled out of the second access opening with the help of the cannula element after the transfer of the fluid from the receptacle into an inserted syringe, wherein the holding force of the holding means is overcome. I.e. herein, the connection between the Luer cone and the Luer connection must be maintained, so that a tensile force can be transmitted for overcoming the holding force of the holding means.

The second access opening is preferably dimensioned such that the cannula element can be removed through the second access opening. For this, the cannula element, preferably together with a syringe which is attached onto the cannula element is pulled out of the second access opening.

In the next step, the syringe with the cannula element can then preferably be inserted into the first access opening and the cannula thereby penetrate into the opening of the cylinder ampule, said ampule being held or fixed in the first receiver. Herein, the cannula preferably pierces a closure, in particular a septum of the cylinder ampule. Herein, the first access opening and the first receiver are preferably configured and arranged such that the cannula element is linearly guided in the first receiver, in order to pierce a septum of the cylinder ampule in a defined manner. Further preferably, a guide is provided, said guide guiding the cannula element such that the cannula penetrates the septum outside the center of the septum. This has the advantage that the septum has not already been pieced by the cannula on filling, where the septum is later pierced in a pen system, so that a good sealing is maintained in this region.

According to a preferred embodiment of the invention, a syringe which is with a Luer cone and which is separate from the housing is a constituent of the filling aid. This syringe is configured such that the Luer cone can engage with the Luer connection of the already described cannula element. The syringe can either be provided as an empty syringe or also be prefilled with a fluid for dissolving a medical or pharmaceutical substance in the receptacle, i.e. for example with a saline solution or water, for injection purposes. This syringe is then applied in the manner which has been described above, in order to transfer a medical or pharmaceutical fluid from the receptacle into a cylinder ampule. The fluid which is contained in the syringe can possibly be firstly pressed into the receptacle, in order to dissolve a dry substance there and to produce the desired fluid. After a sufficient through-mixing, the fluid is then preferably sucked out of the receptacle with the same syringe and the syringe with the cannula element subsequently removed from the second access opening and inserted into the first access opening in the previously described manner, in order to then bring the fluid into the cylinder ampule which is held in the first receiver.

According to a particular embodiment of the invention, a third receiver which is configured for receiving and fixing a syringe is formed in the housing. This third receiver permits the syringe to be inserted into the third receiver after use and to then be disposed of together with the filling aid. The third receiver is preferably only configured for receiving and fixing the syringe, and the cannula element, as described hereinafter, preferably remains in or on the first access opening after use.

The first access opening is preferably dimensioned in a manner such that a cannula element and preferably the previously described cannula element can be inserted into the first receiver through the first access opening. This permits the syringe with the cannula element, after they have been removed from the second access opening, to be inserted into the first access opening, in order to bring or pierce the cannula of the cannula element into the cylinder ampule to be filled.

Further preferably, at least one securing means is arranged in the first receiver, on the first access opening and is configured such that it fixes a cannula element which is inserted through the first access opening and preferably fixes it in a manner in which it cannot be removed again. This, after the bringing of the fluid into the cylinder ampule, permits the syringe to be removed out of the first access opening whilst the cannula element remains fixed there, and be securely kept there for disposal. The securing means is therefore preferably configured such that it can be overcome in one direction on insertion and blocks in the opposite movement direction. This can be achieved for example by way of elastic latching tongues or latching projections which are preferably configured as one piece with at least one housing part. This for example can be the previously described housing or also a component which is connected to the housing, for example the closure element which is described hereinafter.

According to a further preferred embodiment of the invention, the filling aid moreover comprises a closure element which is movable between a first and a second position and which in the first position closes the first access opening and releases the second access opening and in its second position closes the second access opening and releases the first access opening. The closure element serves for a secure handling, since it releases only one access opening in the correct sequence for use. I.e. in the delivered condition, the closure element is preferably situated in its first position, so that a syringe can firstly be inserted into the second access opening. Then, after the syringe has preferably been removed from the second access opening, the closure element can be moved into its second position, so that the first access opening is released and the syringe, again preferably with the attached cannula element, can be inserted into the first access opening. The closure element is preferably likewise configured as an injection molded part of plastic and is movably connected to the housing which is described above. This can preferably be effected by way of latching. It is therefore possible to design the housing and the closure element solely by way of two components, wherein preferably all constituents of the housing which are described above, in particular the holding means, the securing means, the fixation means, arresting and/or clamping are formed as one piece with the housing.

The previously described securing means for the cannula element on the first access opening can preferably be formed by latching hooks or latching tongues on the closure element, so that the cannula element is fixed between the closure element and the housing after insertion into the first access opening.

Further preferably, the closure element comprises at least one releasable block which releasably fixes the closure element in its first and/or second position, wherein the block is preferably releasable with one hand. By way of such a block, one prevents the closure element from being accidentally pushed from the first into the second position. Such a block can be formed for example by a projection on the housing, said projection being arranged on a resilient tongue and, when the closure element is located in its first position, being situated in front of an edge of the closure element, in particular an edge which is at the front in the displacement direction. The projection therefore blocks the movement of the closure element. The projection must then be disengaged from the edge via the resilient tongue, so that the closure element can then be moved, in particular displaced, for moving the closure element. The block can further preferably be configured such that it comes into engagement with the closure element in a suitable manner also in the second position of this closure element, in order to secure the closure element in the second position. For this, a recess or opening, into which the projection of the resilient latching tongue engages, can be formed in the closure element. An arrangement of such a block could also be arranged in a reverse manner such that in the first position of the closure element the projection engages into a recess of the closure element and in the second position of the closure element is situated at an edge of the closure element or of a second recess, said edge being situated at the rear in the displacement direction. Particularly preferably, two such blocks are provided and these are situated at opposite side surfaces of the housing and must be pressed together with the fingers for displacing the closure element.

Further preferably, the closure element is displaceably guided in the housing, in a guide. Herein, the guide is preferably configured in a straight manner and extends transversely to the insertion directions of the syringe into the first and the second access opening. Particularly preferably, the guide and the displacement direction which is defined by it are herein not normal to the mentioned insertion direction, but oblique to it. The effect of this is that the closure element not only displaces transversely to the insertion directions on displacing from the first into the second position, but also by a certain amount in the insertion directions. An opening which in the second position covers the first access opening can be provided in the closure element. This opening simultaneously also serves for guiding the syringe. If the closure element is also moved axially in the insertion direction when it is displaced from the first into the second position, then the guide which is formed by the opening is therefore brought into another axial position. This is advantageous, since usually the cylinder ampule which is to be filled is longer in the axial direction than the mentioned receptacle, in particular a vial. In this manner, it is possible to design the filling aid in a particularly compact manner, in particular in the condition of its delivery, in which the closure element is located in the first position which is envisaged for inserting the syringe into the receptacle. The axial length of the filling aid which is necessary for guiding the syringe for inserting into the cylinder ampule is therefore not created until the displacement of the closure element into its second position, by which means the filling aid lengthens in the axial direction.

The first and the second access opening are preferably arranged on the same side of the housing. This simplifies the handling since it is not necessary to rotate the housing, but the syringe can be brought from the first into the second access opening at the same side.

The first receiver with the first access opening and the second receiver with the second access opening are further preferably arranged and configured such that the insertion directions of the first and the second access opening, along which a cannula element and/or a syringe can be inserted into the access openings and removed from them, run parallel to one another. This also simplifies the handling, since the angular position of the housing does not need to be changed on pulling out and inserting the syringe.

The subject matter of the invention is moreover a method for filling a cylinder ampule with a medical or pharmaceutical fluid whilst using a filling aid, as has been described beforehand. The essentially method steps are described hereinafter. Further details of the method sequence have already been described in the context of the design of the filling aid. These embodiments are referred to with regard to the method.

According to the method, a receptacle with the medical or pharmaceutical fluid which is to be transferred into the cylinder ampule is firstly provided. This receptacle is inserted into the second receiver of the housing of the filling aid or is already inserted there in the delivered condition. A syringe is inserted into the second access opening on the second receiver in the housing in the next step and is brought into fluid-leading connection with the inside of the receptacle. This is preferably effected in a manner such that, as described above, a cannula of a cannula element, said cannula element already being held preassembled in the second receiver, is pierced into the opening of the receptacle. In the next step, the medical or pharmaceutical fluid is transferred out of the receptacle into the syringe. In particular, this can be effected by sucking with the help of the syringe. Alternatively however, one can also provide a receptacle with a plunger, so that the transfer can be effected by way of pressure upon the plunger in the receptacle. After the transfer of the fluid into the syringe, the syringe is removed from the second access opening, wherein preferably a cannula element which is arranged on the syringe is also removed. The syringe, possibly after a previous displacement of a closure element, is subsequently inserted into the first access opening. Herein, inasmuch as is present, the described cannula is pierced into the opening of the cylinder ampule. The medical or pharmaceutical fluid is subsequently pressed out of the syringe into a cylinder ampule which is arranged in the first receiver. The cylinder ampule is preferably already held in the first receiver in a preassembled manner, so that the filling aid is delivered with an assembled cylinder ampule. The cylinder ampule can then be removed from the first receiver after the fluid has been brought out of the syringe into the cylinder ampule, and inserted in the known manner into a carpule syringe or a pen system. As described above, the syringe can then be removed from the first access opening again, wherein a cannula element preferably remains in the receiver. The syringe can then possibly be inserted into a third receiver as has been described above.

According to a particular embodiment of the method, a powder-like, for example freeze-dried medical or pharmaceutical substance can firstly be contained in the receptacle and be dissolved amid the addition of a fluid, in order to produce the mentioned medical or pharmaceutical fluid in the receptacle. For this, a solvent, for example saline solution or water for injection purposes is preferably pressed by the syringe into the receptacle when the syringe has been inserted into the second access opening, whereupon the substance in the receptacle is dissolved by the fluid. This can possibly be effected amid shaking. After the intimate mixing or the dissolving has been effected, the thus produced medical or pharmaceutical fluid is then preferably transferred again into the same syringe as has been described above. The syringe is then removed out of the second access opening in the manner described above and is inserted into the first access opening.

An inventive advantage of the method lies in the fact that the medical or pharmaceutical fluid is pressed from the syringe into the cylinder ampule and is not sucked by the movement of the movable stopper in the cylinder ampule, as is common with the conventional filling of cylinder ampules. This is advantageous since an undesirable foaming of the fluid can be prevented. The receptacle can also be configured such that it comprises a movable plunger which is pressed, in order to press the fluid out of the receptacle into an attached syringe, in order to prevent such a frothing on transfer from the receptacle into the syringe.

The invention is hereinafter described in more detail by way of the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a lateral view of the housing without the closure element;

FIG. 6 is a lateral view of the housing according to FIG. 5 with a view to one of the face sides;

FIG. 7 is a sectioned view through the housing according to FIG. 5 along the line VII in FIG. 6;

FIG. 8 is a perspective view of the closure element;

FIG. 10 is a view showing a step of use of the filling aid according to the invention;

FIG. 11 is a view showing another step of use of the filling aid according to the invention;

FIG. 12 is a view showing another step of use of the filling aid according to the invention;

FIG. 13 is a view showing another step of use of the filling aid according to the invention;

FIG. 14 is a view showing another step of use of the filling aid according to the invention;

FIG. 15 is a view showing another step of use of the filling aid according to the invention;

DESCRIPTION OF THE PREFERRED EMBODIMENTS

Figure 1:
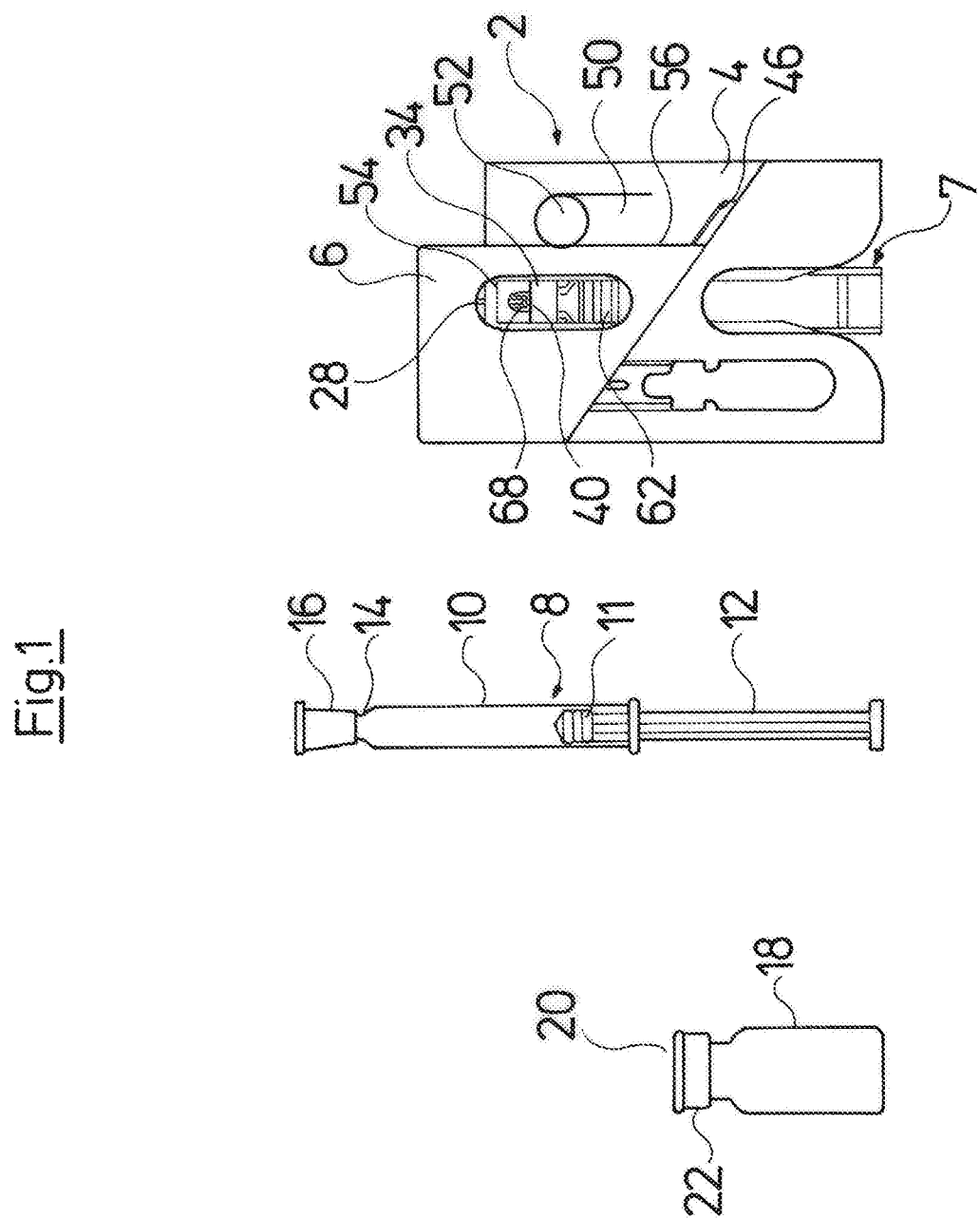
FIG. 1 is a view showing essential parts of a filling aid according to the invention, with a receptacle for a medical or pharmaceutical fluid as well as a cylinder ampule.
Figure 2:
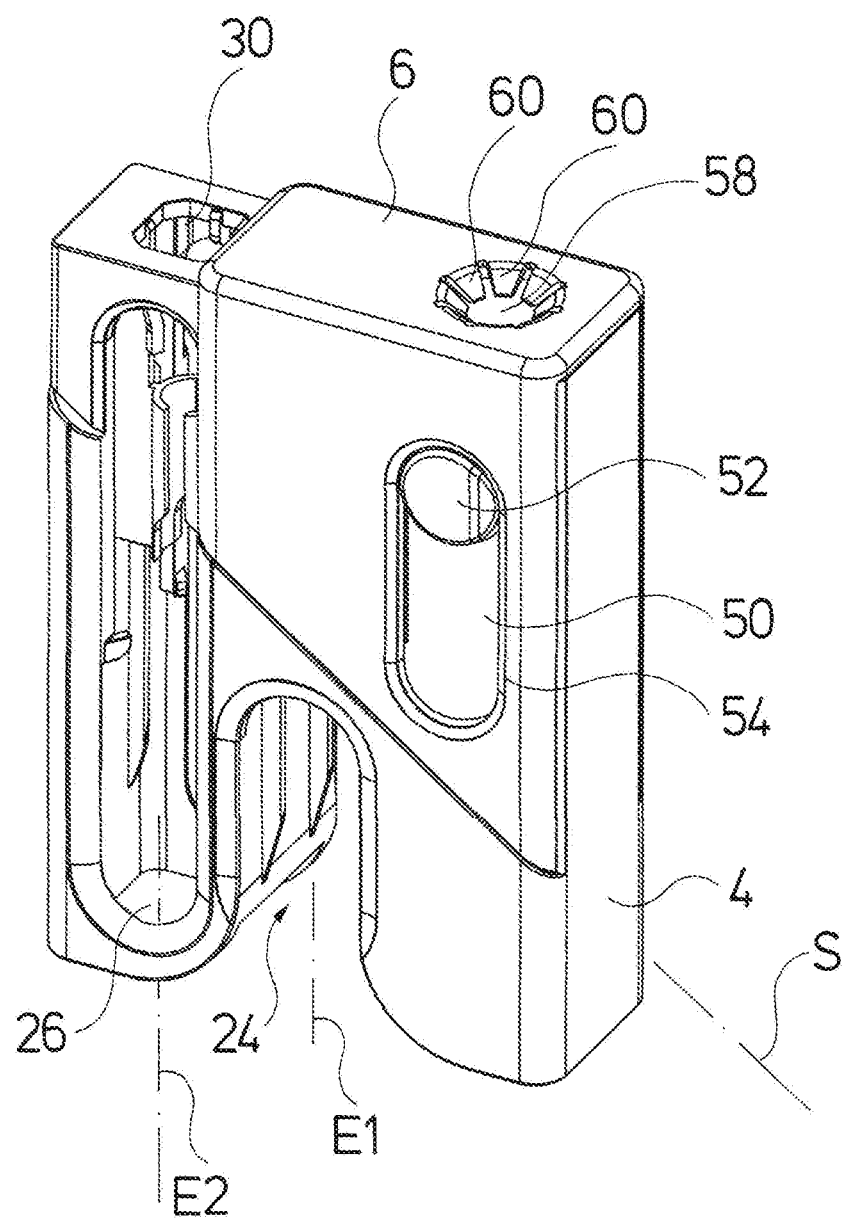
FIG. 2 is a perspective view of the housing of the filling aid with an attached closure element.
Figure 3:
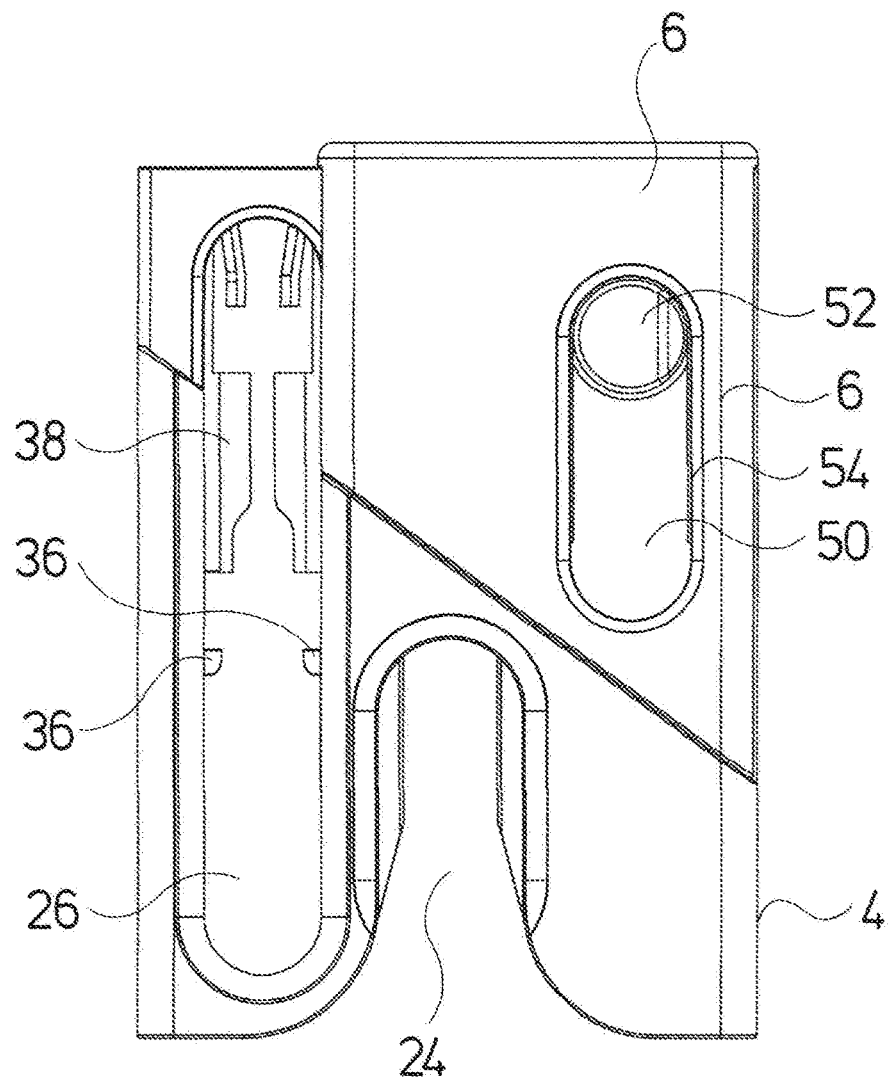
FIG. 3 is a lateral view of the housing according to FIG. 2.
Figure 4:
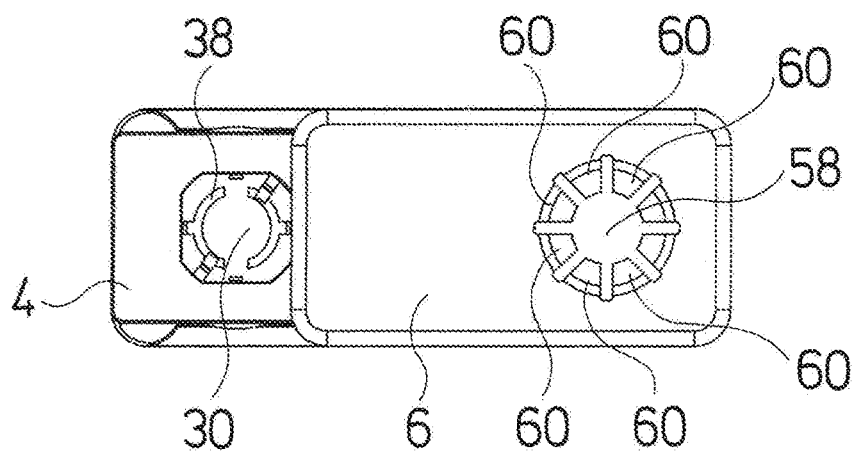
FIG. 4 is a plan view of the housing according to FIG. 3.

Referring to the drawings, the filling aid which is shown here as an example comprises two essential components, specifically, on the one hand a holding device 2 which is formed from a housing 4 with a closure element 6 which is arranged thereon, and on the other hand a syringe 8. The holding device 2 serves for receiving a cylinder ampule 7 which is to be filled. The syringe 8 in the usual manner is formed from a cylinder 10 with a plunger 11 which is movable therein via a plunger rod 12. The syringe 8 at its end comprises a Luer cone 14, on which a cap 16 is attached in the example shown in FIG. 1.

The filling aid according to the invention serves for bringing a medical or pharmaceutical fluid out of a receptacle 18 into the cylinder ampule 7. The receptacle 18 which is shown here is a common vial or injection vial, which is closed at its upper side by a plug or a septum 20. Surrounding the septum 20, a collar 22 is formed on the receptacle 18. The housing 4 comprises a first receiver 24 and a second receiver 26, wherein the first receiver is configured for receiving the cylinder ampule 7 and the second receiver 26 for receiving the receptacle 18, i.e. are shaped and dimensioned accordingly. The first receiver 24 and the second receiver 26 are open to the same side of the housing 4 and have insertion directions E1 and E2 which are parallel to one another and along which the cylinder ampule 7 and the receptacle 18 are inserted into the first receiver 24 and the second receiver 26 respectively. A first access opening 28 which opens to a face side of the housing 4 which is opposite to the insertion direction E1 is arranged on the first receiver 24. The second receiver 26 accordingly comprises a second access opening 30 which opens to the same side as the first access opening 28.

Resilient latching tongues 32 which are formed as one piece with the housing 4 are arranged in the first receiver 24 close to the first access opening 28. These latching tongues 32 are arranged and configured such that they can encompass a collar 34 which surrounds a plug or septum of the cylinder ampule 7, in order to releasably fix the cylinder ampule 7 in the receiver 24. When the cylinder ampule 7 is fixed in the receiver 24 in this manner, the opening of the cylinder ampule 7 which is closed by the septum lies opposite the first access opening 28.

The latching tongues 32 which form fixation means are arranged and configured such that given an adequately large force action in the insertion direction E1, they deform radially outwards away from the first access opening 28, so that the collar 34 can pass the latching tongues 32 and the cylinder ampule can be removed from the first receiver 24.

Fixation means in the form of latching tongues 36 are arranged in the second receiver 26 and are dimensioned and arranged such that they can engage behind the collar 22 of the receptacle 18, in order to fix the receptacle 18 in the second receiver 26. Herein, the latching tongues 36 with their projections can be configured such that the receptacle 18 cannot be removed again out of the second receiver 26, i.e. the latching tongues 36 only widen once on insertion of the receptacle into the second receiver 26 and are not envisaged to release the receptacle 18 again. Alternatively, the latching tongues 36 can however also be configured in accordance with the latching tongues 32, so that it is possible to remove the receptacle 18 again.

Figure 9:
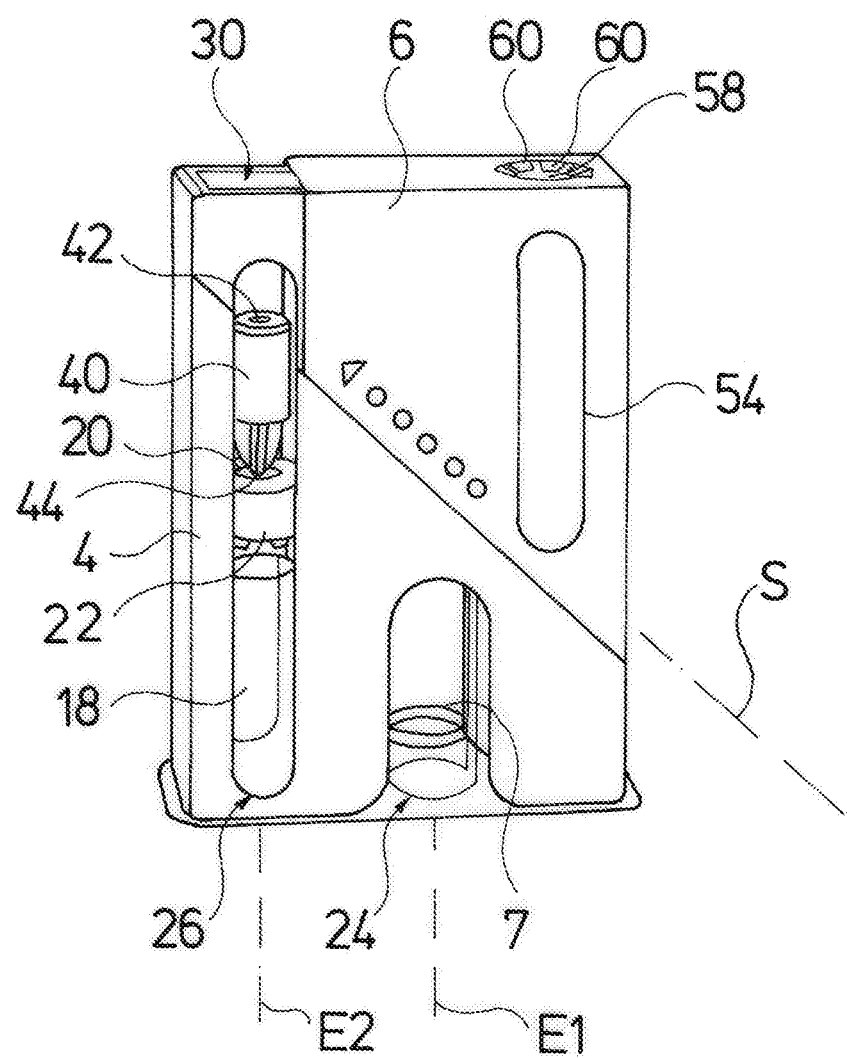
FIG. 9 is a perspective view of the filling aid with an inserted cylinder ampule and an inserted receptacle.

A holding means 38 in the form of a clamping is formed in the second receiver 26, between the latching tongues 36 and the second access opening 30. The holding means 38 serves for receiving and fixing a cannula element 40. Herein, the cannula element 40 is guided in the insertion direction E2 in an axial displaceable manner by the holding means 38. The cannula element 40 at its end which faces the second access opening 30 comprises a Luer connection 42 and at its opposite end comprises a cannula 44. The cannula element 40 is displaceable in the insertion direction E2 between a first position which is shown in the detail A1 in FIG. 12, and a second position which is shown in the detail A2 in FIG. 12. In the second position, the cannula 44 penetrates into the septum 20 of the receptacle 18, as is shown for example in FIG. 9. The second access opening 30 is dimensioned such that the cannula element 40 is removable from the second access opening 30.

The closure element 6 is configured as a slider which is displaceable on the housing 4 and which engages over the housing 4 at two sides. I.e. the closure element 6 has a U-shaped cross section and engages over the housing 4 on two side surfaces which are away from one another. The movement or displacement direction S of the closure element 6 extends transversely to the insertion directions E1 and E2. Herein, the displacement direction S does not run normally, but obliquely to the insertion directions E1 and E2. For this, the housing 4 at each of its two side surfaces which are away from one another comprises a guide groove 46 which extends in the displacement direction S. The closure element 6 on each of its two inner surfaces which face one another comprises a projection 48 (only one is visible in FIG. 8) which engages into the guide grooves 46.

The closure element 6 is configured such that in a first position which is shown in the FIGS. 2 to 4 and 9, it closes the first access opening 28 and releases the second access opening 30. In this position, the closure element 6 is secured against unintended displacement by way of a block. This block is formed by two resilient tongues 50 on two side surfaces of the housing 4 which are away from one another. The tongues 50 each comprise outwardly projecting projections 52 at their free ends. In the first position of the slider, these projections 52 each engage into an opening 54 on the closure element 6. It is necessary to press together the two projections 52 from the outside so that they disengage from the opening 54, in order to be able to displace the closure element 6 into its second position. In the second position, the tongues 50 then spring back outwards again and the projections 52 come to bear on a side edge 56, as is shown for example in FIG. 1. The closure element 6 is therefore secured in its second position. In this second position, an opening 58 which is formed on the face side of the closure element 6 lies opposite the first access opening 28. The opening 58 comprises spring tongues 60 on its periphery, said spring tongues forming a securing means for holding the cannula element 40. The opening 58 and the spring tongues 60 are dimensioned such that the cannula element 40 can pass the opening 58 amid radial widening of the spring tongues 60. Once the cannula element 40 has passed the opening 58, the spring tongues 60 spring back radially inwards again and prevent a return movement of the cannula element 40.

The manner of functioning of the filling aid according to the invention is now explained by way of FIGS. 10 to 20. In this embodiment example, the receptacle 18 is prefilled with a powder-like medical or pharmaceutical substance. As is shown in FIG. 10, the holding device 2 is delivered in a condition, in which the closure element is located in its first position. The cylinder ampule 7 is moreover preassembled in the housing 4, in the first receiver 24. There, it is held in the manner described above by way of latching tongues 32. In this condition, a movable plunger 62 is held in the position which is shown in FIG. 1, i.e. close to the opening or the septum of the cylinder ampule 7 which is held by the collar 34. The cannula element 40 is moreover preassembled in the housing 4, wherein it is firstly located in its first position which is shown in the detail A1 in FIG. 12, i.e. in a position which faces the second access opening 30. In this condition, the receptacle 18 is inserted into the second receiver 26 in the second insertion direction E2, wherein the latching tongues 36 radially widen, so that the collar 22 can pass the projections of the latching tongues 36 and be subsequently embraced by the projections of the latching tongues 36, so that the receptacle 18 is fixed in the second receiver 26.

In the next step, after removal of the cap 16, the syringe 8, as is shown in FIG. 11, is inserted into the second access opening 30. Herein, the Luer cone 14 of the syringe 8 engages with the Luer connection 42 of the cannula element 40. In this example, the syringe 8 is prefilled with a fluid for dissolving the medical or pharmaceutical substance, for example a saline solution or water, for injection purposes.

Once the syringe 8 with its Luer cone 14 has engaged with the cannula element 40, as is shown in FIG. 12, the syringe 8 is advanced further in the insertion direction E2, so that the cannula element 40 is moved into its second position which is distanced further from the second access opening 30, as is shown in the detail A2 in FIG. 12. In this position, the cannula 44 pierces the septum 20 of the receptacle 18. In the next step, the plunger rod 12 of the syringe 8 is displaced and the contents of the syringe 8 is therefore emptied through the cannula element 40 into the receptacle 18, as is shown in FIG. 13. The substance is therefore dissolved in the receptacle 18, wherein the holding device 2, i.e. the housing 4 can be possibly shaken for this. In the next step, as is shown in FIG. 14, the holding device 2 with the inserted syringe 8 is turned around, so that the plunger rod 12 is directed downwards. The syringe 8 is pulled in this condition, so that the contents of the receptacle 18 which is now a medical or pharmaceutical fluid is drawn into the syringe 8.

In the next step, as is shown in FIG. 15, the holding device 2 is turned over again and the syringe 8 is withdrawn together with the cannula element 40 out of the second access opening in the insertion direction E2, wherein the cannula 44 is pulled out of the septum 20. For this, it is necessary for the holding force in the holding means 38 to be smaller than the clamping force between the Luer cone 14 and the Luer connection 42.

Figure 16A:
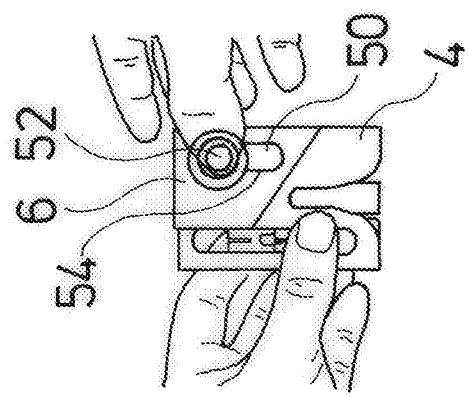
FIG. 16 is a view showing another step of use of the filling aid according to the invention.
Figure 16B:
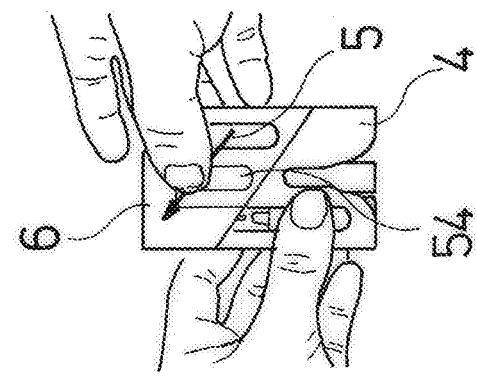
Figure 17:
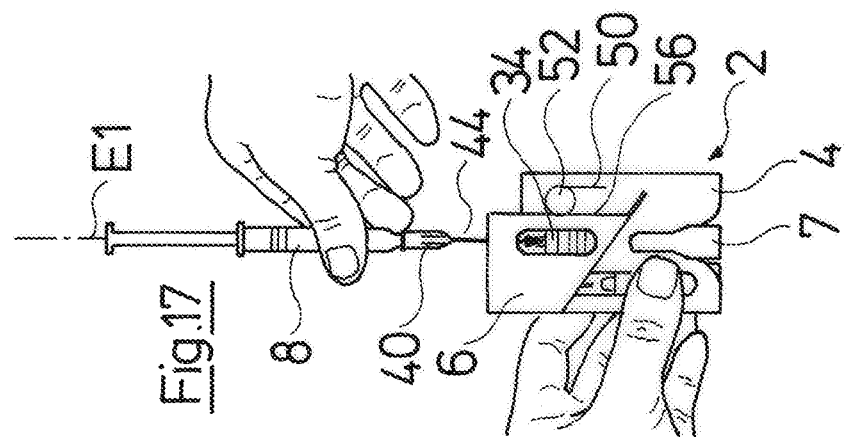
FIG. 17 is a view showing another step of use of the filling aid according to the invention.

In the next step, as is shown in FIG. 16a and FIG. 16b, the closure element 6 is displaced on the housing 4 along the displacement direction S. For this, as is shown in FIG. 16a, the projections 52 (only the projection situated at the front side is visible in FIG. 16a, and a second, identically formed projection 52 is situated on the rear side) are firstly pressed together, so that the projections 52 disengage from the openings 54. The closure element 6 can subsequently be displaced in the displacement direction S, as is shown in FIG. 16b. Herein, a one-handed operation is possible. I.e. the pressing-together of the projections 52 and the displacement of the closure element 6 can be effected without embracing by a hand, since the closure element 6 can be held in the region of the openings 54 for displacing this element. The closure element 6 thus gets into its second position which is shown in FIG. 17. In this position, the projections 52 on the tongues 50 spring back outwards, so that they come to bear on the side edges 56 of the closure element 6 and secure this in the shown second position.

Figure 19:
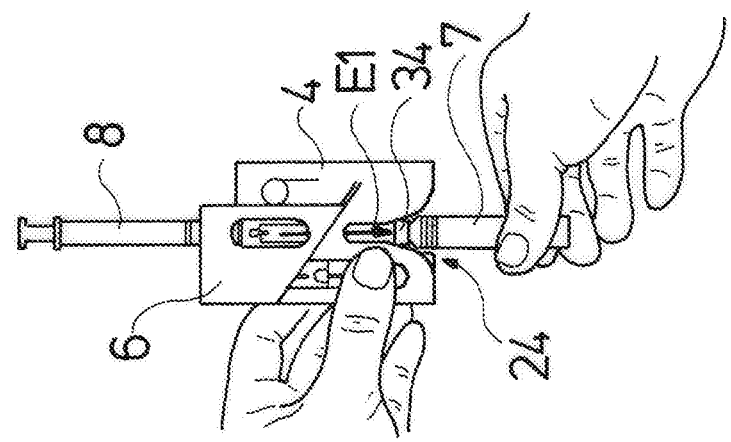
FIG. 19 is a view showing another step of use of the filling aid according to the invention.
Figure 18:
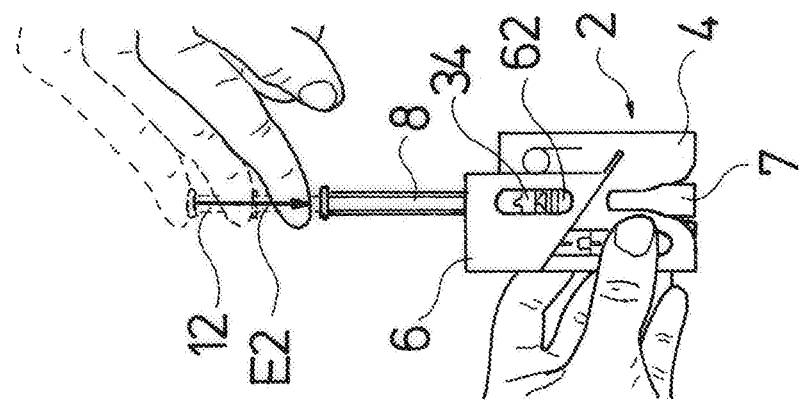
FIG. 18 is a view showing another step of use of the filling aid according to the invention.
Figure 21:
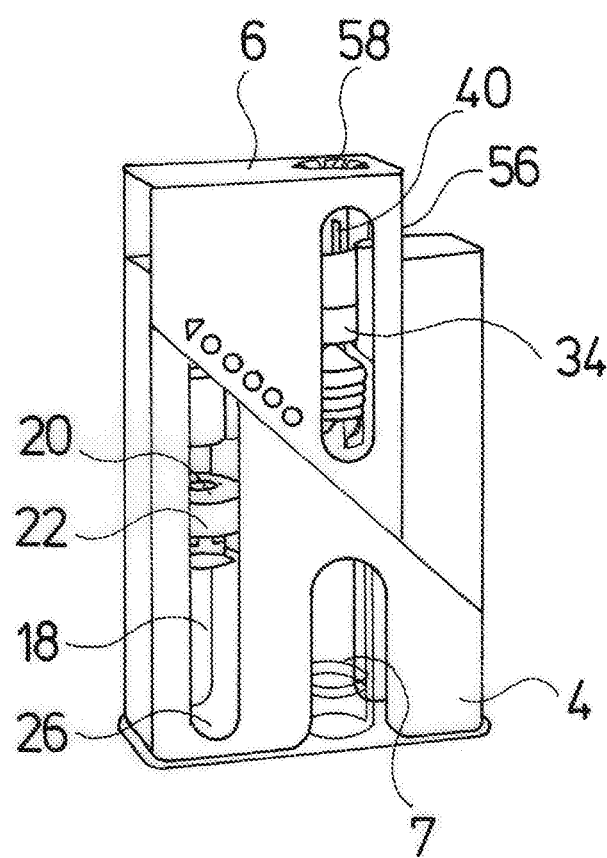
FIG. 21 is a perspective view of the filling aid after filling the cylinder ampule.

In this position, the syringe 8 with the cannula element 40 with the cannula 44 in front is firstly inserted into the opening 58 on the closure element 6 in the insertion direction E1 and subsequently inserted into the first access opening 28 of the housing 4 which now lies therebelow. Herein, the cannula element 40 passes the spring tongues 60 on the opening 58 in the previously described manner. The cannula 44 simultaneously enters through the closure or the septum into the cylinder ampule 7. In this condition, the plunger rod 12 of the syringe 8 is now pushed in the insertion direction E2 and the contents of the syringe 8 are pressed or brought into the cylinder ampule 7, as is shown in FIG. 18. Herein, the plunger 62 in the cylinder ampule 7 displaces to the end of this ampule which is away from its opening. As is shown in FIG. 19, the cylinder ampule 7 is pulled out of the first receiver 24 in the insertion direction E1 in the next step. Herein, the latching tongues 32 widen radially, so that the collar 34 of the cylinder ampule 7 can pass the projections of the latching tongues 32. The syringe 8 thereby firstly remains in the first access opening 28.

The first access opening 28 comprises a guide 68 for the cannula element 40, said guide 40 guiding the cannula element 40 such that the cannula 44 enters the closure or a septum of the cylinder ampule 7 at a defined position. Herein, the guide is preferably selected such that the cannula 44 enters the septum of the cylinder ampule 7 in an out-of-center manner. I.e. the guide 68 with its longitudinal axis or middle axis is slightly radially offset with respect to the middle axis of the first receiver 24. This has the effect that the septum of the cylinder ampule 7 is pieced at a location other than will be the case later on using the cylinder ampule 7 in a pen system.

Figure 20:
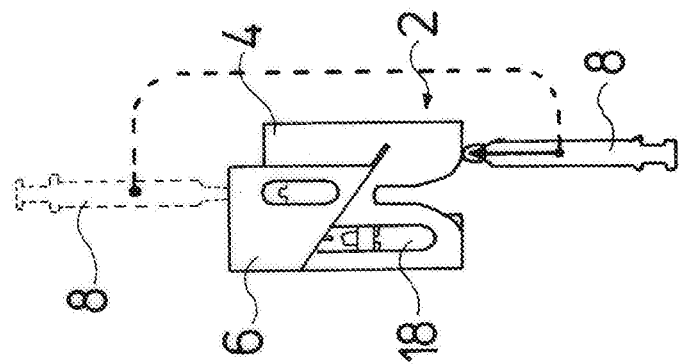
FIG. 20 is a view showing another step of use of the filling aid according to the invention.

As is shown in FIG. 20, the syringe 8 can subsequently be removed again out of the opening 58, wherein the Luer cone 14 of the syringe 8 thereby releases again from the Luer lock 42 of the cannula element 40, since the cannula element 40 is held back by the spring tongues 60 as is described above. The syringe 8 can subsequently be inserted into a third receiver 64 (see FIG. 7) in the housing 4. A clamping element 66 which in its shape is adapted to the Luer cone 14 such that this is clamped in the clamping element 66 is formed in the third receiver 64. The syringe 8 is then fixed in the housing 4 in this condition. The cannula element 40 is simultaneously fixed between the closure element 6 and the housing 4 in the described manner and the emptied receptacle 18 is fixed in the second receiver 26 again. The holding device 2 then together with the cannula element 40 of the syringe 8 and the receptacle 18 can then be disposed of in this condition.

While specific embodiments of the invention have been shown and described in detail to illustrate the application of the principles of the invention, it will be understood that the invention may be embodied otherwise without departing from such principles.

The invention claimed is:

1. A filling aid for filling a cylinder ampule with a medical or pharmaceutical fluid, the filling aid comprising a common housing comprising:
   a first receiver configured for receiving the cylinder ampule to be filled;
   a second receiver configured for receiving a receptacle containing a medical or pharmaceutical substance;
   a first access opening formed on the first receiver and arranged such that the first access opening lies opposite an opening of the cylinder ampule with the cylinder ampule inserted into the first receiver;
   a second access opening formed on the second receiver and arranged such that the second access opening lies opposite an opening of the receptacle with the receptacle inserted into the second receiver, wherein a cannula element, which comprises a cannula and a Luer connection, is releasably held in the second receiver, wherein the Luer connection of the cannula element faces the second access opening and the cannula is directed such that the cannula penetrates into the receptacle which is inserted into the second receiver; and
   a syringe which is separate from the common housing and which syringe comprises a Luer configured to engage the Luer connection of the cannula element.

2. A filling aid according to claim 1, further comprising fixation means arranged in the first receiver and configured to releasably fix the cylinder ampule in the first receiver.

3. A filling aid according to claim 2, wherein the cylinder ampule is preassembled and releasably fixed in the first receiver by the fixation means and is removable out of the first receiver.

4. A filling aid according to claim 1, further comprising fixation means arranged in the second receiver, said fixation means being configured to releasably fix the receptacle, containing the medical or pharmaceutical substance, in the second receiver.

5. A filling aid according to claim 1, wherein the second access opening is dimensioned such that the cannula element is removable through the second access opening.

6. A filling aid according to claim 1, further comprising at least one holding means for releasably fixing the cannula element, the at least one holding means being arranged in the second receiver, wherein the holding means produces a holding force in a longitudinal direction of the cannula, said holding force being smaller than a force transmitted by the Luer connection in the longitudinal direction.

7. A filling aid according to claim 1, wherein the common housing comprises a third receiver configured to receive and fix the syringe.

8. A filling aid according to claim 1, further comprising a closure element movable between a first and a second position and which closing element, in the first position, closes the first access opening and releases the second access opening and in a second position closes the second access opening and releases the first access opening.

9. A filling aid according to claim 8, wherein the closure element comprises at least one releasable block which releasably fixes the closure element in the first position or in the second position or in both the first position and the second position, wherein the block is releasable with one hand.

10. A filling aid according to claim 1, wherein the first access opening and the second access opening are arranged on a same side of the housing.

11. A filling aid according to claim 1, wherein the first receiver with the first access opening and the second receiver with the second access opening are configured such that insertion directions of the first access opening and of the second access opening along which a cannula element and/or a syringe inserted into the respective access openings, run parallel to one another.

12. A filling aid for filling a cylinder ampule with a medical or pharmaceutical fluid, the filling aid comprising a common housing comprising:
   a first receiver configured for receiving the cylinder ampule to be filled;
   a second receiver configured for receiving a receptacle containing a medical or pharmaceutical substance;
   a first access opening formed on the first receiver and arranged such that the first access opening lies opposite an opening of the cylinder ampule with the cylinder ampule inserted into the first receiver; and
   a second access opening formed on the second receiver and arranged such that the second access opening lies opposite an opening of the receptacle with the receptacle inserted into the second receiver, wherein a cannula element, which comprises a cannula and a Luer connection, is releasably held in the second receiver, wherein the Luer connection of the cannula element faces the second access opening and the cannula is directed such that the cannula penetrates into the receptacle which is inserted into the second receiver, wherein the first access opening is dimensioned such that the cannula element is insertable through the first access opening into the first receiver.

13. A filling aid according to claim 12, wherein at least one securing means is arranged on the first access opening, in the first receiver, said securing means being configured to non-removably fix the cannula element which is inserted through the first access opening.

14. A filling aid according to claim 13, wherein the at least one securing means is configured as a latching element comprising a latching tongue.

15. A method for filling a cylinder ampule with a medical or pharmaceutical fluid, the method comprising the steps of:
providing a filling aid comprising a common housing comprising a first receiver configured for receiving the cylinder ampule to be filled, a second receiver configured for receiving a receptacle containing the medical or pharmaceutical substance, a first access opening formed on the first receiver and arranged such that the first access opening lies opposite an opening of the cylinder ampule when the cylinder ampule is inserted into the first receiver, and a second access opening formed on the second receiver and arranged such that the second access opening lies opposite an opening of the receptacle with the receptacle inserted into the second receiver; and the following further steps, successively:
positioning the receptacle with the medical or pharmaceutical fluid which is to be brought into the cylinder ampule in the second receiver;
inserting a syringe into the second access opening;
sucking the medical or pharmaceutical fluid out of the receptacle into the syringe;
removing the syringe from the second access opening and inserting the syringe into the first access opening; and
bringing the medical or pharmaceutical fluid out of the syringe into the cylinder ampule which is arranged in the first receiver.

16. A method according to claim 15, wherein a powder-like medical or pharmaceutical substance is firstly contained in the receptacle and is dissolved amid the addition of a fluid, in order to thus produce the mentioned medical or pharmaceutical fluid in the receptacle.

17. A method according to claim 16, wherein the powder-like medical or pharmaceutical substance is firstly contained in the receptacle, the syringe is filled with a fluid for dissolving the substance before the insertion into the second access opening, the fluid is brought out of the syringe into the receptacle after the insertion of the syringe into the second access opening, in order to dissolve the powder-like substance and thus form the medical or pharmaceutical fluid, and the fluid is subsequently sucked back into the same syringe, in order to bring the fluid into the cylinder ampule.

* * * * *